(12) United States Patent
Thrier et al.

(10) Patent No.: US 6,468,408 B2
(45) Date of Patent: Oct. 22, 2002

(54) POLYMERIC ELECTROLYTE

(75) Inventors: Rolf Thrier, Effretikon (CH); Stephan Buschor, Chur (CH); Heiner Bührer, Hittnau (CH); Hannes Bühler, Amden (CH)

(73) Assignee: Hamilton Bonaduz AG, Bonaduz (CH)

( * ) Notice: Subject to any disclaimer, the term of this patent is extended or adjusted under 35 U.S.C. 154(b) by 0 days.

(21) Appl. No.: 09/777,825

(22) Filed: Feb. 8, 2001

(65) Prior Publication Data
US 2001/0025790 A1 Oct. 4, 2001

(30) Foreign Application Priority Data
Feb. 10, 2000 (EP) .............................................. 00102774

(51) Int. Cl.[7] ........................ G01N 27/30; G01N 27/333
(52) U.S. Cl. ........................ 204/435; 204/416; 204/421
(58) Field of Search ................................ 204/435, 416, 204/418, 419, 421–429

(56) References Cited

U.S. PATENT DOCUMENTS

| 3,798,570 | A |   | 3/1974  | Niedrach         |
| 3,912,614 | A |   | 10/1975 | Spracklen et al. |
| 4,214,968 | A | * | 7/1980  | Battaglia et al. |
| 4,568,444 | A |   | 2/1986  | Nakamura et al.  |
| 4,774,029 | A |   | 9/1988  | Poulin           |
| 4,959,138 | A | * | 9/1990  | Brinkmann et al. |
| 5,360,529 | A |   | 11/1994 | Edwards et al.   |

FOREIGN PATENT DOCUMENTS

EP    0 807 817 A1    11/1997

* cited by examiner

Primary Examiner—T. Tung
(74) Attorney, Agent, or Firm—Fulbright & Jaworski L.L.P.

(57) ABSTRACT

The invention relates to a polymeric electrolyte which is part of an electrochemical reference electrode and which is used in potentiometric and amperometric sensors. The polymeric electrolyte is a hydrogel which is stable in a large pH-range and stable against organic solvents.

21 Claims, 1 Drawing Sheet

FIG. 1
FIG. 2
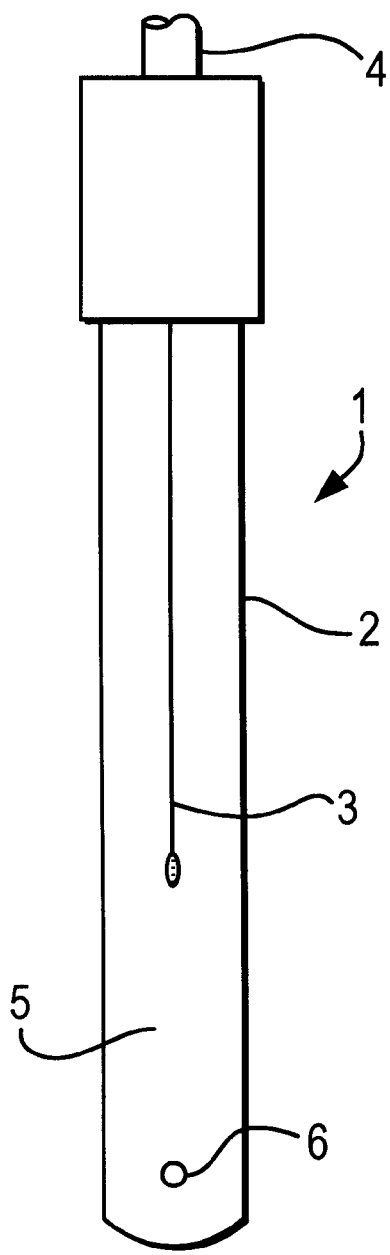
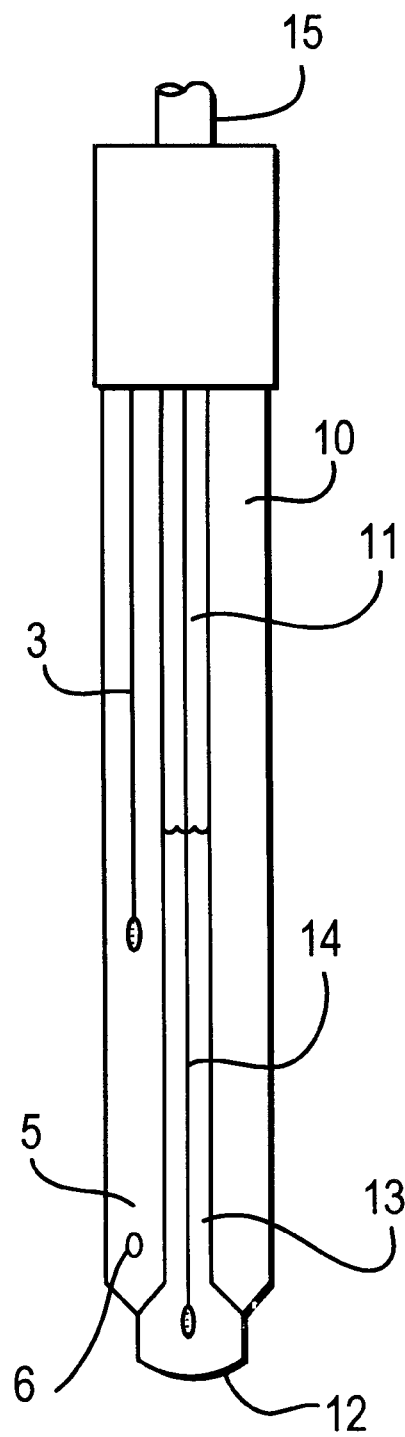

POLYMERIC ELECTROLYTE

DESCRIPTION

The invention relates to a polymeric electrolyte which is part of an electrochemical reference electrode and which is used in potentiometric and amperometric sensors. The polymeric electrolyte is a hydrogel which is stable in a large pH-range and stable against organic solvents.

Electrochemical reference electrodes in combination with potentiometric or amperometric electrodes for the determination of e.g. pH value are known. In most cases so-called combination electrodes are used, wherein the reference electrode is concentrically arranged around the inner sensing electrode. A liquid junction is responsible for the electrolytic contact between the reference electrolyte inside of the reference electrode and the measuring solution. The reference electrode is usually a concentrated aqueous solution of potassium chloride.

There is a transport of material at every liquid junction. If the concentration of materials is not equal on both sides of the liquid junction, diffusion processes occur for creating a balance of all concentrations of material. Additional convective transport of material is present, if there is a pressure difference on both sides of the junction. A third reason for transport of material is migration caused by a potential difference at the liquid junction. The last type of transport only comprises electrically charged particles.

Most of the electrochemical reference electrodes are equipped with a porous ceramic plug serving as a liquid junction. This plug also called diaphragm is mounted in the outer shaft of the electrode either by melting, glueing or pressing. There are different types of diaphragm such as ground glass joints, cotton fibres, twisted metal filaments or wires, porous plastic plugs, wooden pins. In general porous materials can be used for the liquid junction.

A further group of liquid junctions are particularly modified plastics. U.S. Pat. No. 4,002,547 describes a compact consisting of Teflon, glass fibres and KCl powder. During operation some solid KCl is dissolved by the storage or measuring solution resulting in micro pores filled with solution along the glass fibres providing an electrochemical junction to the inner reference electrolyte. These micro pores act as liquid junction. U.S. Pat. No. 5,152,882 describes a further example, wherein glass fibres are embedded in epoxy resin. This composite plastic material is not a liquid junction. After grinding the surface, the glass fibres contact the measuring solution. Due to the lack of a chemical bonding there is a micro gap between the epoxy resin and the glass fibre, which can be filled with solution. Thus, a liquid junction between the inner electrolyte and the measuring solution is formed, as soon as the gaps are filled with solution.

All the above described liquid junctions are characterized by the presence of very fine pores or gaps between the reference electrolyte and the measuring solution. They must be small in order to minimize the exchange of solution between the measuring solution and the reference electrolyte through the liquid junction. If the exchange of solution is too high, the chemical composition of the reference electrolyte changes too rapidly. Parallel thereto, the potential of the reference electrode is subject to change, which causes early recalibration or even sensor failure resulting in a reduced sensor life time.

However, the small pores of the liquid junction may be contaminated rapidly in many solutions. The pores or gaps of the liquid junction may be clogged by substances of the measuring solution or by a reaction between the reference electrolyte and the measuring solution. This contamination changes the surface of the liquid junction and may lead to great adsorption potentials. These error potentials up to 60 mV result in measuring errors up to a 1 pH unit. Especially high errors occur in solutions containing proteins or suspended materials. Generally speaking, chemical reaction or physical adsorption of material at the liquid junction often result in measuring errors. The contamination of the liquid junction or diaphragm represents the most severe problem of potentiometric measurements in laboratory and field.

U.S. Pat. No. 4,959,138 attempts to solve the problem of liquid junction contamination by replacing the many small pores by just one single opening. The liquid or viscous reference electrolyte of conventional electrodes therefore has to be replaced by a polymeric electrolyte to prevent the convective flow of the electrolyte. Hydrogels consisting of crosslinked polyacrylamide are used as polymeric electrolyte. In order to improve the life time of the reference electrode, the hydrogel additionally contains suspended KCl powder and silicagel. The liquid junction of this reference electrode consists just of a hole filled with polymeric electrolyte. In case of this reference electrode the measuring solution is in direct contact with the polymeric electrolyte. The risk of error potentials due to a contamination of the liquid junction is decisively smaller, since there is only one big opening.

However, the polymer of U.S. Pat. No. 4,959,138 has some severe drawbacks: It shrinks irreversibly in acidic media and the sensor has to be replaced quite often. Furthermore, in the field of pharmaceutical and chemical industry often partially aqueous or non-aqueous solutions occur, i.e. organic solvents are used. The polymeric electrolyte based on polyacrylamide shrinks in the presence of such solvents so that the sensor is no longer functioning. A further disadvantage of the polymer described in U.S. Pat. No. 4,959,138 is its brittleness resulting in cracks after repeated or large temperature changes. These cracks in the polymer might lead to an interrupted electrical circuit. A further severe disadvantage of electrodes with a polymeric electrolyte based on polyacrylamide is the poisoning character of the monomer acrylamide. Working with acrylamide is very dangerous and undesired, particularly, since unreacted monomers remain from each polymerization and may diffuse through the liquid junction into the measuring solution.

U.S. Pat. No. 4,774,029 describes an electrically conductive polymer, which is produced by reacting a tetraalkylammonium acrylate with an acrylic resin and which is impermeable to liquids.

U.S. Pat. No. 5,360,529 describes a reference electrode having a gelled electrolyte solution comprising a polymer containing acrylamide units substituted with a group which lowers the polymer's tendency to hydrolyse. Preferably used is a polymer based on tris(hydroxymethyl)methyl acrylamide units. Such polymers, however, are unstable in the presence of organic solvents.

It was therefore an object of the present invention to provide a reference electrode, wherein the above mentioned drawbacks of the prior art are eliminated at least to a great extent. On the one hand the reference electrode must withstand contaminations and, on the other hand, however, avoid the problems involved with known polymeric electrolytes. Particularly, the reference electrode shall function also in acidic solutions as well as in the presence of organic solvents and provide correct measuring results This object is accomplished according to the present invention by providing an electrochemical reference electrode containing an electrolyte comprising a polymer based on monomers selected from N-substituted acrylamides and/or methacrylates, wherein the polymeric electrolytes or hydrogels according to the invention show a considerably higher stability towards acids and organic solvents compared to prior art polymeric electrolytes. Furthermore, N-substituted acrylamides and methacrylates are less hazardous and poisonous substances than acrylamide.

The polymeric electrolyte according to the present invention is obtainable by polymerization or copolymerization of said monomers in a suitable housing of a reference electrode. Preferably the polymerization takes place as usual by adding a suitable radical starter or/and at elevated temperature in the presence of a suitable liquid phase, preferably the liquid phase of the reference electrode. Preferably the polymeric electrolyte is made by dissolving all substances in the reference electrode. Apart from the indicated monomers, the polymeric electrolyte may optionally also contain further suitable monomers. Preferably, essentially no acrylamide is applied, i.e. the content of acrylamide is less than 10 Mol %, particularly less than 5 Mol %, more preferably less than 1 Mol % and particularly preferably less than 0.1 Mol % with respect to the total amount of monomers used. Most preferred the polymeric electrolyte is produced without the use of acrylamide and is free of acrylamide. Preferably the content of suitable additional monomers is not more than 10 Mol % with respect to the total amount of the monomers.

The N-substituted acrylamides are preferably selected so that they neither have a fully hydrophilic nor a fully hydrophobic character. Preferred examples are N,N-dimethyl-acrylamide (DMA), N-[tris(hydroxymethyl)methyl] acrylamide N-hydroxymethyl-acrylamide, N-hydroxyethylacrylamide, N-glycerol-acrylamide and combinations thereof. More hydrophilic N-substituted acrylamides such as N-(2-hydroxy-1,1-bis-hydroxymethyl-ethyl)-2-methacrylamide(trisacrylamide) or more hydrophobic N-substituted acrylamides such as N,N-diethyl-acrylamide (DEA) alone are not universally applicable and less suited for certain applications. E.g. trisacrylamide results in an acid resistant hydrogel, however, it has a strong tendency towards shrinking in the presence of organic solvents due to its hydrophobic character. Thus, when used alone, trisacrylamide does not form an electrolyte according to the present invention. DEA is resistant against acids and solvents, the corresponding polymer structure, however, is only little soluble in aqueous solutions. Hence, no homogenous hydrogels are obtained. Such hydrophilic or/and hydrophobic N-substituted acrylamides can only be used in combination with one of the preferred substances, as indicated above. Particularly preferred N,N-dimethylacrylamide is used as N-substituted acrylamide, optionally in combination with one or more further N-substituted acrylamides.

Further, the polymeric electrolyte according to the invention can be based on methacrylate monomers. Preferred methacrylate monomers are methacrylate esters with alcohols having 3 or more hydroxy groups, wherein one hydroxyl group is used for the ester binding with methacrylic acid so that the resulting methacrylate monomer is glycol-methacrylate or 2,3-dihydroxyproplymethacrylate (DPM), respectively. DPM is an unstable monomer, hence it is preferably produced in situ from glycidymethacrylate by hydrolysis. Also preferred are polymeric electrolytes on the basis of a methacrylate ester having at least two free hydroxyl groups, e.g. DPM, and one or more or further methacrylates as comonomers. As comonomers methacrylates with less than 2 free hydroxyl groups may be used.

Further polymeric electrolytes are suitable that contain at least one N-substituted acrylamide and at least one methacrylate as comonomer, wherein in this embodiment also methacrylates containing less than 2 free hydroxyl groups may be used as comonomers. Preferred are e.g. polymeric electrolytes based on N,N-dimethylacrylamide and one or more methacrylates, e.g. 2-hydroxymethylmethacrylate, 2-hydroxyethylmethacrylate (HEMA), 2,3-dihydroxyproylmethacrylate and combinations thereof. The content of methacrylate monomers is preferably 1–30 mol % with respect to the total amount of monomers of the polymeric electrolyte. Further preferred are polymers based on methacrylate ester having at least two free hydroxyl groups, e.g. 2,3-dihydroxypropylmethacrylate and one or more N-subtituted acrylamides as comonomers.

In order to decrease the brittleness suitable substances, e.g. amorphous silic acid or fumed silicon dioxide (Airosil) may be added to the polymeric electrolyte. The amount of fumed silicon dioxide is preferably 0.1–10 wt. % with respect to the total weight of solid particles of the polymeric electrolyte. Fumed silicon dioxide with a specific surface of 50–500 $m^2/g$ is preferred.

In addition to hydrogel, the electrolyte of the reference electrode further contains a liquid phase. Preferably the polymeric electrolyte is based on a liquid reference electrolyte. Normally a concentrated aqueous salt solution is used, wherein the salts can be selected from alkali metal salts having anorganic or organic anions. Suitable salts are KCl, NaCl, LiCl, $KNO_3$, $KClO_4$, Na-formiate, Li-acetate and mixtures thereof. An aqueous solution of 3M KCl is preferred.

In certain applications, however, it is advantageous to use a mixture of such a concentrated aqueous salt solution and an organic solvent, which is preferably miscible with the salt solution. Thus, the aqueous salt solution can be replaced by a partly aqueous electrolyte solution containing an organic solvent. Preferred organic solvents are glycerol, ethyleneglycol, methanol, ethanol, n-propanol, isopropanol, acetone and mixtures thereof. Such partly aqueous electrolytes, e.g. 50% (v/v) 3M KCl solution and 50% (v/v) glycerol reduce the risk of a diaphragm contamination by precipitated proteins. In general the amount of organic solvent preferably is in the range from 10–90% (v/v), more preferably from 30–70% (v/v).

The reference electrodes according to the present invention generally can be constructed in any form known from the prior art, e.g. as standard reference electrodes. However, it is preferred to use reference electrodes having an open liquid junction to the surrounding medium. Most preferred the liquid junction consists of one single hole or opening. Thereby problems associated with contamination of the liquid junctions in form of small pores or gaps can be avoided. The direct contact between the polymeric electrolyte and the measuring solution greatly reduces the risk of building up a contaminated liquid junction. The reference electrode according to the present invention is used in combination with a suitable sensing electrode in form of a sensor, e.g. a potentiometric or amperometric sensor in order to determine physico-chemical or electrochemical parameters. This is usally done in a liquid medium such as liquid samples. The reference electrode according to the present invention shows an excellent stability in acidic and in at least partly organic solutions.

The following examples together with two figures are intended to further illustrate the invention.

FIG. 1 shows a schematic cross-section of an electrochemical reference electrode. This electrochemical measuring cell 1 exhibits an outer tubular electrode shaft 2, which may consist of glass or plastic. In electrode shaft 2 a bleeder electrode 3 is arranged, connection 4 of which leads to the exterior. For example chloridized silver wire serves as bleeder electrode 3. The interior of reference electrode 1 is filled with polymeric electrolyte 5. Lower opening 6 serves as liquid junction between the measuring solution and the polymeric electrolyte. The not yet polymerized electrolyte is introduced via lower opening 6 into the interior by using vacuum. Then the reference electrolyte is polymerized at room temperature or at elevated temperature until it is solidified. After solidification the polymerized reference electrolyte 5 is no longer able to exit via opening 6. Opening 6 exhibits a diameter of e.g. 0.5 to 1 mm. Instead of one single opening 6, several openings may also be arranged in electrode shaft 2.

FIG. 2 shows a so-called combination electrode, wherein reference electrode 10 is concentrically arranged around a sensing electrode 11. Reference electrode 10 again consists of a bleeder electrode 3, polymeric electrolyte 5 and an opening and liquid junction, respectively, 6. Sensing electrode 10 consists of an ion selective membrane 12, e.g. a pH glass diaphragm, interior electrolyte 13 and bleeder electrode 14. Both bleeder electrodes 3 and 14 are in contact with the exterior by a coaxial cable.

The production of polymeric electrolyte 5 is performed according to the following examples:

EXAMPLES

EXAMPLE 1 (Comparison)

Polymeric Electrolyte According to U.S. Pat. No. 4,959,138 in 3M KCl 20 g acrylamide, 1,4 g N,N'-methylene-bis-acrylamide and 0.12 ml N,N,N',N'-tetraethylenediamine are dissolved in 100 ml 3M KCl solution. In parallel 0.07 g ammoniumpersulfate are dissolved in 100 ml 3M KCl solution. After mixing, the reference electrodes are filled with this solution by using vacuum. The filled reference electrodes are stored in the polymerization solution. After some hours at room temperature the polymerization is complete. The reference electrodes are stored in 3M KCl solution.

EXAMPLE 2

Polymeric Electrolyte on the Basis of N,N-Dimethyl-acrylamide (DMA) in 3M KCl 11.5 g DMA, 0,4 g N,N'-methylene-bis-acrylamide, 0.07 ml N,N,N',N'-tetraethylenediamine, 0.01 g ammoniumpersulfate and 1 g highly dispersed fumed silicon dioxide (Degussa Airosil 200, having a surface of 200 m2 per gram) are dissolved in 61 ml 3 M KCl solution. The solution is stirred intensively for 30 minutes at room temperature. Then the reference electrodes are filled as in example 1. The polymerization was completed at 60° C. after 2 hours. The reference electrodes are stored in 3 M KCl solution.

EXAMPLE 3

Copolymeric Electrolyte on the Basis of DMA and HEMA in 1.5 M KCl (60% Glycerol)

23 g DMA, 1.2 g HEMA, 0,8 g N,N'-methylene-bis-acrylamide, 0.14 ml N,N,N',N'-tetraethylenediamine, 0.02 g ammoniumpersulfate and 1.2 g highly dispersed fumed silicon dioxide are dissolved in 95 ml 1.5 M KCl solution containing 60% glycerol. The solution is stirred intensively for 30 minutes at room temperature. The reference electrodes are filled as in example 1. The polymerization was completed at 60° C. after 2 hours. The reference electrodes are stored in 1.5 M KCl solution containing 60% glycerol.

EXAMPLE 4

Polymeric Electrolyte on the Basis of Glycerol-methacrylate (DPM) in 1.5 M KCl (60% Glycerol)

0.035 g sulfuric acid and 0.025 g hydrochinone are dissolved in 64 g water and heated up to 90° C. Within 3 h a total of 50 g glycidylmethacrylate are slowly added to the stirred hot solution. After an additional hour at 90° C. the solution is cooled down to 40° C. The water is removed at about 40 mbar. A clear viscous solution of the monomer glycerol-methacrylate is obtained.

100 g of the above glycerol-methacrylate, 2 g N,N'-methylene-bisacrylamide and 1.0 ml N,N,N',N'-tetraethylenediamine are dissolved in 150 ml 1.5 M KCl solution containing 60% glycerol at 50° C. After cooling down the mixture to room temperature 6 g highly dispersed silicic acid are added. The solution is stirred intensively for 30 minutes. 0.5 g ammoniumpersulfate. are added to the stirred solution. Then the reference electrodes are filled as in example 1. The polymerization was completed at 70° C. after 2 hours. The reference electrodes are stored in 1.5 M KCl solution containing 60% glycerol.

EXAMPLE 5

Polymeric Electrolyte on the Basis of DMA in $KCl+KNO_3$

Certain applications require a polymeric electrolyte with a small concentration of KCl. A further salt is added to increase the conductivity and ionic strength. It is preferred to add an equitransferent salt such as potassium nitrate, potassium perchlorate, lithium acetate or sodium formiate in order to keep the diffusion potentials at the liquid junction low.

15.6 g DMA, 0.8 g HEMA, 0.53 g N,N'-methylene-bis-acrylamide, 0.1 ml N,N,N',N'-tetraethylenediamine, 0.29 g ammoniumpersulfate and 1 g highly dispersed fumed silicon dioxide (Airosil 200) are dissolved in 82 g solution containing 2 M $KNO_3$ and 0.1 M KCl. The solution is stirred for 30 minutes at room temperature. The reference electrodes are filled as in example 1. The polymerization was completed at 60° C. after 2 hours. The reference electrodes are stored in the $KNO_3$–KCl solution.

Test of the polymeric electrolytes in 1 M HCl at 80° C. during 1 week:

Polymeric electrolyte acc. to Ex. 1: shrinking, hydrogel completely destroyed

Polymeric electrolyte acc. to Ex. 2: swelling

Polymeric electrolyte acc. to Ex. 3: swelling

Polymeric electrolyte acc. to Ex. 4: unchanged

Polymeric electrolyte acc. to Ex. 5: minimal shrinking

Test of the polymeric electrolytes in 80% ethanol at 50° C. during 1 week:

Polymeric electrolyte acc. to Ex. 1: strong shrinking

Polymeric electrolyte acc. to Ex. 2: swelling

Polymeric electrolyte acc. to Ex. 3: swelling

Polymeric electrolyte acc. to Ex. 4: small swelling

Polymeric electrolyte acc. to Ex. 5: minimal swelling

Test of the polymeric electrolytes in 80% isopropanol at 50° C. during 1 week:
- Polymeric electrolyte acc. to Ex. 1: strong shrinking
- Polymeric electrolyte acc. to Ex. 2: unchanged
- Polymeric electrolyte acc. to Ex. 3: unchanged
- Polymeric electrolyte acc. to Ex. 4: small swelling
- Polymeric electrolyte acc. to Ex. 5: unchanged swelling Test of the polymeric electrolytes in 80% acetone at 50° C. during 1 week:
- Polymeric electrolyte acc. to Ex. 1: strong shrinking
- Polymeric electrolyte acc. to Ex. 2: slight swelling
- Polymeric electrolyte acc. to Ex. 3: slight swelling
- Polymeric electrolyte acc. to Ex. 4: unchanged
- Polymeric electrolyte acc. to Ex. 5: minimal swelling These examples clearly show the advantages of the polymeric electrolytes according to the present invention (examples 2–5) compared to the conventional hydrogel based on acrylamide (example 1).

What is claimed is:

1. An electrochemical reference electrode comprising an electrolyte comprising a polymer comprising at least one monomer selected from the group consisting of N-substituted acrylamides and methacrylates, wherein said N-substituted N-acrylamide is selected from the group consisting of N,N-dimethyl-acrylamide, N,N-diethyl-acrylamide, N-hydroxymethyl-acrylamide and N-hydroxyethyl-acrylamide, and wherein said methacrylate is selected from the group consisting of 2-hydroxymethyl-methacrylate, 2-hydroxyethylmethacrylate, glycerolmethacrylate and 2,3-dihydroxypropyl-methacrylate; wherein said electrolyte is stable against organic solvents.

2. The electrochemical reference electrode according to claim 1, wherein the N-substituted acrylamide is N,N-dimethyl-acrylamide.

3. The electrochemical reference electrode according to claim 1 wherein said polymer comprises N,N-dimethyltcrylamide and at least one additional N-substituted acrylamide as the monomers.

4. The electrochemical reference electrode according to claim 3, wherein said polymer comprises an N-substituted acrylamide and at least one of 2-hydroxymethylnethacrylate, 2-hydroxyethylmethacrylate, and 2,3-dihydroxypropylmethacrylate.

5. The electrochemical reference electrode according to claim 4 wherein the percentage of methacrylate monomers is in the range of 1–30 mol % with respect to the total amount of monomers.

6. The electrochemical reference electrode according to claim 4 wherein said polymer comprises 2,3-dihydroxypropylmethacrylate and at least one N-substituted acrylamide as monomers.

7. The electrochemical reference electrode according to claim 1, wherein said methacrylate is 2,3-dihydroxypropyl-methacrylate.

8. The electrochemical reference electrode according to claim 1, wherein said polymer comprises 2,3-dihydroxypropyl-methacrylate and at least one additional methacrylates.

9. The electrochemical reference electrode according to claim 1, wherein said polymer comprises N,N-dimethyl-acrylamide and at least one methacrylate as monomers.

10. The electrochemical reference electrode according to claim 9 wherein the percentage of methacrylate monomers is in the range of 1–30 mol % with respect to the total amount of monomers.

11. The electrochemical reference electrode according to claim 1, wherein said electrolyte contains 0.1–10wt. % of at least one silicon compound selected from the group consisting of amorphous silicic acid and fumed silica with respect to the total weight of solid substances.

12. The electrochemical reference electrode according to claim 11, wherein the silicic acid or fumed silica has a specific surface of 50–500 m$^2$/g.

13. The electrochemical reference electrode according to claim 1, wherein the electrolyte further comprises a concentrated aqueous salt solution.

14. The electrochemical reference electrode according to claim 1, wherein the electrolyte further comprises a mixture of a concentrated salt solution and an organic solvent.

15. The electrochemical reference electrode according to claim 14, wherein said salt is at least one salt selected from the group consisting of KCl, NaCl, LiCl, KNO$_3$, KClO$_4$, sodium formiate and lithium-acetate.

16. The electrochemical reference electrode according to claim 14, wherein said orgacic solvent is at least one solvent selected from glycerol, ethyleneglycol, methanol, ethanol, n-propanol, isopropanol and acetone.

17. The electrochemical reference electrode according to claim 1, wherein an open liquid junction with a surrounding medium is provided.

18. A potentiometric or amperometric sensor comprising the electrochemical reference electrode of claim 1.

19. A method of determination of pysico-chemical parameters of liquid media to be analyzed comprising contacting the electrochemical reference electrode of claim 1 with a liquid media to be analyzed.

20. The method of claim 19, wherein said liquid media is acidic.

21. The method of claim 19, wherein said liquid media comprises at least a portion of an organic media.

* * * * *